United States Patent [19]

Gabbay

[11] 4,279,248
[45] Jul. 21, 1981

[54] STERNUM CLOSURE DEVICE AND PROCEDURE FOR USING SAME

[76] Inventor: Shlomo Gabbay, 2433 Tiemann Ave., Bronx, N.Y. 10469

[21] Appl. No.: 59,364

[22] Filed: Jul. 20, 1979

[51] Int. Cl.³ .............................................. A61B 17/00
[52] U.S. Cl. ............................... 128/92 EA; 128/346; 128/334 R; 24/243 B
[58] Field of Search ............... 128/334 R, 334 C, 335, 128/336, 337, 346; 24/92 EA, 93 FA, 81 FT, 243 B, 243 E, 263 A, 202 S

[56] References Cited

U.S. PATENT DOCUMENTS

| 2,426,975 | 9/1947 | Roach | 24/243 B |
| 2,583,896 | 1/1952 | Siebrandt | 128/346 |

Primary Examiner—Norman Yudkoff
Attorney, Agent, or Firm—Bierman & Bierman

[57] ABSTRACT

A sternum closure device is provided by a series of upper and lower clamping devices which are held by a series of threaded rod from a support. The device is used for holding together the halves of a split sternum which has previously been cut to expose the chest cavity as required for example in heart operations. The lower clamping device is positioned beneath the sternum which is then pulled together in a known manner. The upper clamping device or clamps are then pushed down on a threaded rod to cooperate with the lower clamping device with the two clamping members forced toward one another into the sternum halves by nuts on the threaded rods. The unused portion of the rods and the support are then discarded. Different forms of under-clamps are described. A sternum closure procedure utilizing the sternum closure device is also disclosed.

11 Claims, 8 Drawing Figures

STERNUM CLOSURE DEVICE AND PROCEDURE FOR USING SAME

This invention is directed to a new sternum closure device of the type used in post-operative procedures, such as, for example, after the chest has been opened for the performance of various kinds of heart or by-pass operations.

In accordance with procedures presently in use after an operation in the chest cavity which requires that the latter be exposed by first splitting the sternum as by sawing and then spreading the split sternum and attached rib structure to expose the chest cavity, the cavity must be reclosed and bound together in as normal a manner as possible. This presently entails first bringing the separated sternum halves together by means of clamps, generally called approximators, drilling a series of spaced holes in the sternum adjacent the joined sections, pulling and holding the joined sections together by wire sutures pulled tight through these holes. The wires are tied together and left in the sternum, being covered by the patient's skin.

The procedure above described, while generally used and accepted in some 120,000 heart operations alone performed annually in the United States today, has serious disadvantages. The first of the disadvantages and one which in many cases can be critical to the life of the patient is the time required for the closing procedure, which presently may vary from one-half hour to one-and-a-half hours. If the sternum is soft, the force needed to hold the chest cavity together may result in the wire sutures tearing through the bone; the placement of the holes through which the sutures pass is extremely important. These factors contribute to the amount of time required for the procedure.

It is self-evident that the longer the chest cavity is exposed, the greater the danger of infection, and the length of any operative procedure is deleterious to the recovery of the patient.

The use of wire sutures, which after being twisted together must be cut off, sometimes leaves sharp ends which are not easily covered by the patient's skin.

The use of wire stutures for reestablishing the chest structure presents further problems in the event the chest cavity has to be reopened, a procedure which not unseldom takes place, for example, in the replacement of heart valves, with the initial replacement proving to be unsatisfactory for various reasons. In such event, the individual wire sutures must then all be cut, and the sternum which by then may have rehealed together, be resawed with the ever-present danger to underlying organs, such as the heart itself.

As will be presently described, the dangers and disadvantages of present procedures as above set forth are obviated by the present invention which may shorten sternum closure time from as much as one-and-one-half hours to ten or fifteen minutes, and in one form of the present invention automatically leaves a protective strip in situ, a strip which will shield the underlying organs in the event the chest has to be reopened.

Briefly, in place of the present suturing procedure, my invention utilizes a series of longitudinally spaced, generally U-shaped clamps cooperating with one another below and above the sternum, the upstanding ends of such clamps being sufficiently sharp to bite into the sternum when the clamps are forced together as by a rotatable nut threaded on a supporting rod. After clamping action has been obtained, the unused portion of the rod is cut off and the portion remaining covered by the patient's skin. Individual clamps may be used above and below the sternum, but in one form of the invention, while individual clamps are used above, or exteriorly, the lower clamp beneath the sternum may consist of a single strip of U-shape configuration with sharp edges and spaced holes to receive the bolts supporting the individual exterior clamp, or a thin flexible strip running the length of the sternum to which individual under-clamps have been attached.

In conformity with the above, it is therefore an object of this invention to provide a sternum closure device which is not only completely safe for the purpose in mind, but one which will substantially reduce the time required by the sternum closure procedures now available.

A second object of this invention is the provision of a sternum closure device which will not only reduce the time required for the sternum closure procedure, but when left in situ automatically provides a safety feature against the damage of internal organs if reopening of the sternum is required.

A further object of the invention is to provide a sternum closure clamp which will replace sutures and their attendant disadvantages.

These and other objects and advantages of my invention will become apparent from the more detailed description of the preferred forms thereof and as illustrated in the attached drawings, in which.

Figure 1:
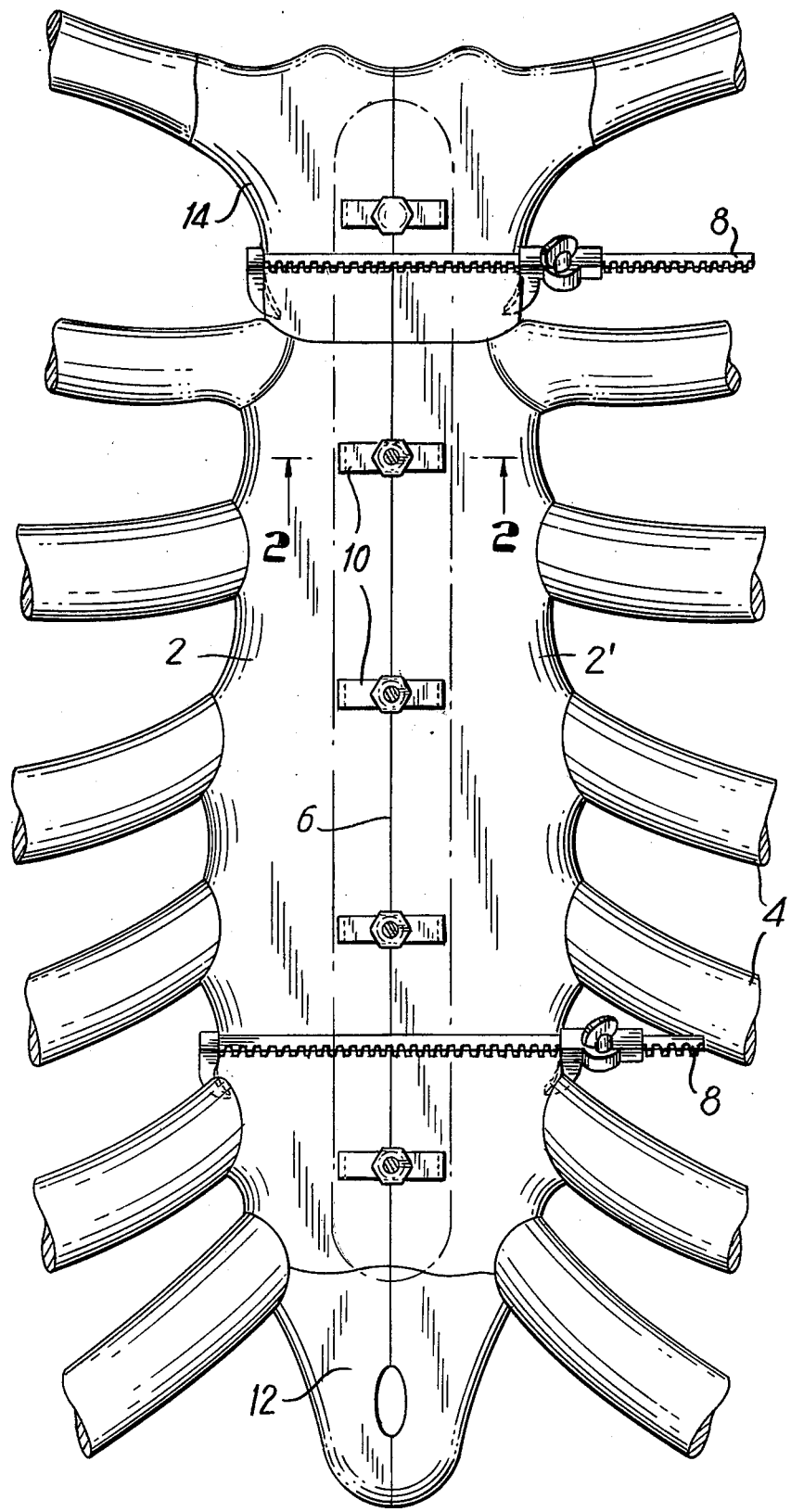
FIG. 1 is a plan view of an exposed sternum illustrating the application of a closure device in accordance with this invention.

As previously discussed, it is necessary in performing an operation within the chest cavity, for example in the replacement of a heart valve or in a by-pass operation, to open the cavity by first sawing through or otherwise splitting the sternum, after which through the use of instruments such as a rib spreader, the rib cage is opened up to expose the organs requiring treatment. At the end of the operation, the chest cavity is closed, and as explained above, it is important that this closure procedure be accomplished in the minimum amount of time. FIG. 1 is illustrative of sternum halves 2 and 2' with attached ribs 4 which have been pulled together along cut 6 by two approximators 8, a procedure well known in the art. However, as illustrative of this invention, instead of the wire sutures heretofore used for thereafter holding the sternum halves together after the approximators have been removed, a series of clamps 10 cooperating with clamping means (not shown) beneath the sternum, bite into the bone structure to finalize the closure procedure. The number and spacing of such clamps depends upon the length of the sternum and the resistance of the rib cage, but in any event they should extend from just adjacent the xiphoid process 12 into the manubrium 14. Clamps 10 will hold the sternum halves in tight contact, one with the other for subsequent healing, and will ordinarily remain in place. For that reason such clamps should be made of a material such as stainless steel which will provide sufficient mechanical strength and at the same time is acceptable to body tissue.

Figure 2:
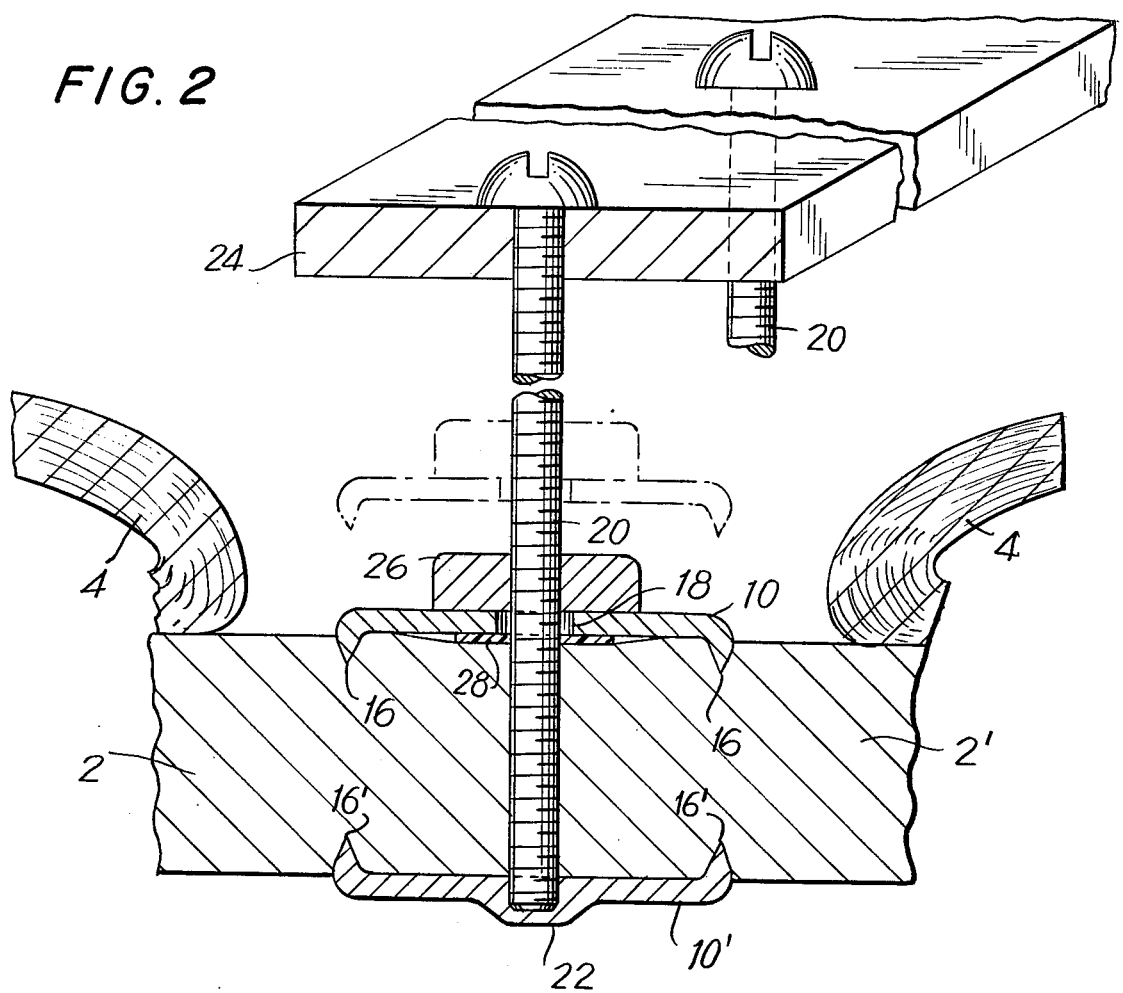
FIG. 2 is an enlarged cross-sectional view along the lines 2—2 of FIG. 1 showing details of a preferred form of the sternum closure device.

One form of my invention is illustrated in greater detail in FIG. 2 in which one of the series of upper-clamps 10 is in the form of a narrow strap having sharp downturned edges 16. The strap is provided with an enlarged central opening 18 permitting it to ride freely on the threaded rod 20. Under-clamp 10' is substantially identical in size and shape with upper-clamp 10, but in this case sharp edges 16' are upturned to bite into the sternum from below, and the center of the clamp is slightly enlarged at 22 to form a seat for the lower end of rod 20 and provided with internal threads into which the said lower end is tightly screwed.

The manner in which my sternum closure device is used will now be described. Since a series of spaced clamps is desired, as aforedescribed, they are supported from rod 20 in longitudinally spaced relation from a holder or support 24 which may be a longitudinal strip of preferably plastic material into which the rods are threaded at spaced intervals. In addition to supporting clamps 10 and 10', each rod is provided with a clamping nut 26. Beneath each upper-clamp 10, there is moreover provided a simple thin clamp holding device 28 formed of some suitable absorbable material which will initially hold the upper-clamp 10 in a suspended position as shown in dotted lines.

Accordingly, as the rib cage is being pulled together as by approximators 8, before final closure, the physician holding the clamps by support 24 positions the necessary number of lower clamps 10' longitudinally along and transversely of the sternum, the upper-clamps 10 being held on the rod but above the sternum as previously described. The sternum halves are then brought together in final position by the approximators and immediately thereafter the upper-clamps 10 are pushed into place and nuts 26 tightened by any suitable device so that aligned clamps 10 and 10' hold the closed sternum tightly together. The proper tightening of these clamps can be accomplished in ten or fifteen minutes as contrasted with present wire suturing procedures which may take one-half to one-and-one-half hours.

Figure 3:
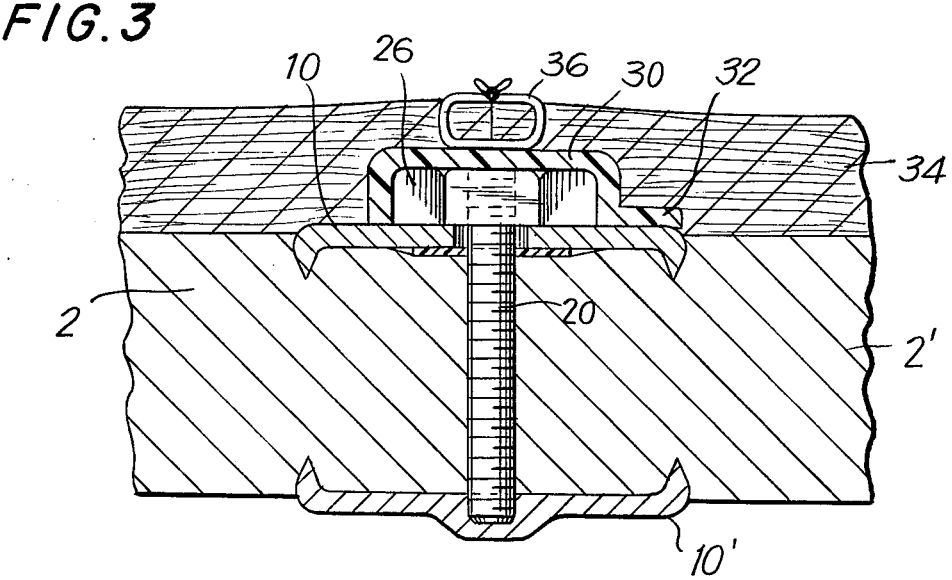
FIG. 3 is an enlarged cross-sectional view of a portion of the sternum with the closure device in place.

The sternum as finally closed will have the general appearance shown in FIG. 3, in which sternum halves 2 and 2' are now tightly bound together by clamps 10 and 10' united as one clamping unit on rod 20 by nut 26, the individual rods having been cut and the unused portions thereof removed. To cover the sharp edges of the nut and the exposed end of the rod, it is preferable to cover the same by a thin press-fit stainless steel cap 30 which for easy removal (if necessary) may be provided with a projecting lip 32. The patient's skin 34 is drawn over the cap and sutured as at 36.

Figure 4:
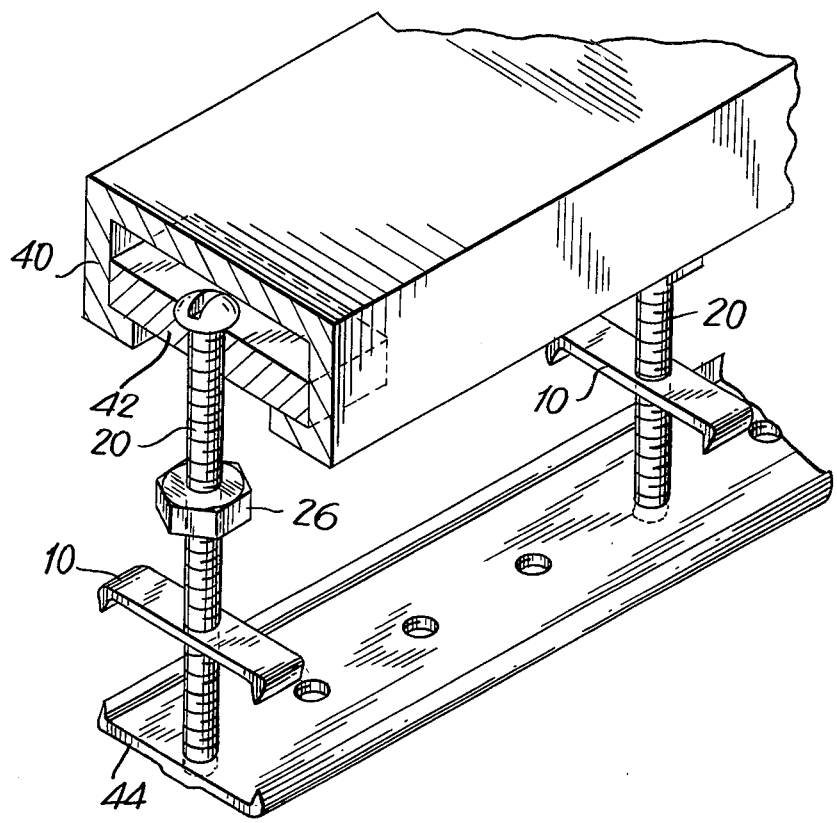
FIG. 4 is an enlarged view in perspective and partially in cross section illustrating a modified form of sternum closure device.
Figure 5:
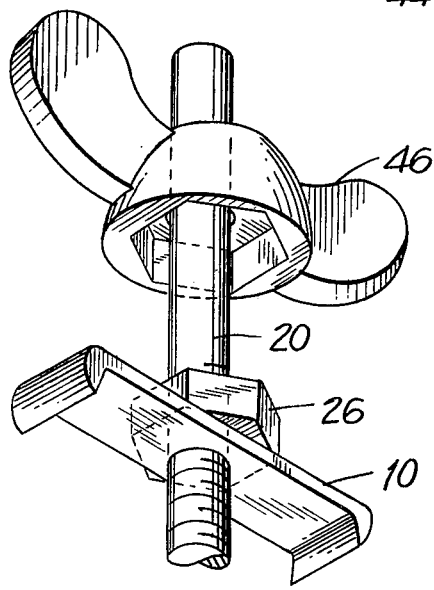
FIG. 5 is an enlarged view in perspective of a modified detail of the sternum closure device.

It will be noted that the clamp holder or support 24 by its very nature supports the clamps at fixed intervals which may not always be suitable for the specific sternum structure of the patient. Variable spacing provides the flexibility which the surgeon or physician may require and to that end the form of invention shown in FIG. 4 utilizes a hollow under-cut support 40 in which the clamp shafts are supported in individually slidable mounts 42. Such slidable mounts may be used either with individual lower clamps 10', as shown in FIG. 2, or the latter may be replaced by a lower clamp 44 of a single continuous strip of the same cross-sectional configuration as the individual clamps, and having a series of spaced threaded openings into which the lower ends of rods 20 will be appropriately screwed. The clamping procedure previously described will in either case essentially be followed.

Keeping in mind that time is an important factor in any sternum closure procedure, tightening of nuts 26 can be facilitated by loosely mounting on rod above each nut, winged device 46 having a hollowed internal section conforming to the external shape of nut 26. Thus each clamp will have its own tightening device which may be reused or discarded after tightening has been completed and the upper portion of the rod removed.

Figure 6:
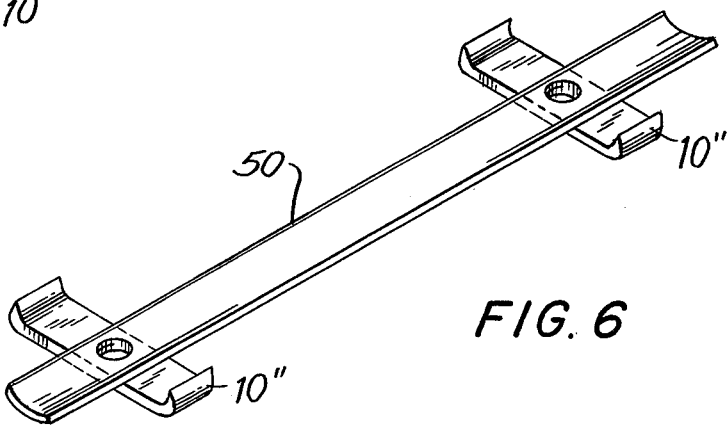
FIG. 6 is a view in perspective of still a partial further modification of the sternum closure device.
Figure 7:
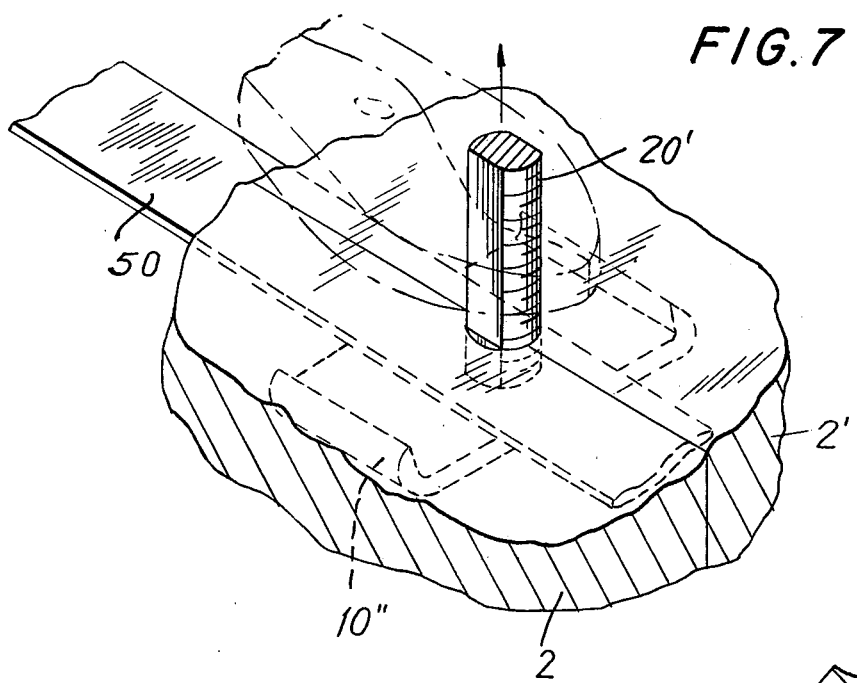
FIG. 7 is an enlarged view in perspective and partially in cross-section illustrating a special form of removable rod used with a clamp forming part of the sternum closure device.
Figure 8:
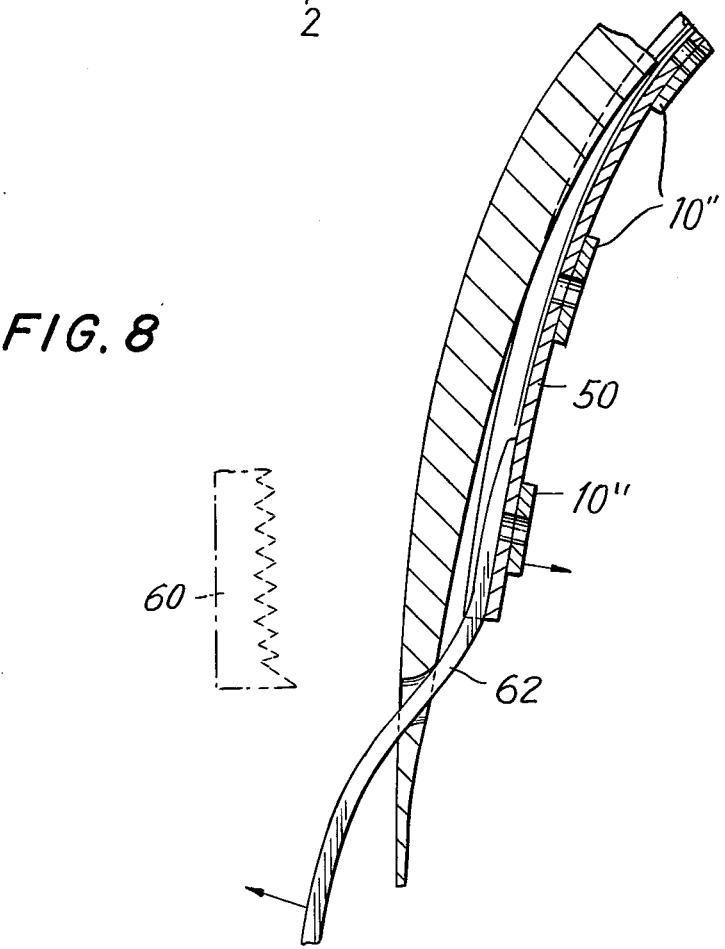
FIG. 8 is a longitudinal section of a sternum illustrating a procedure for removing a form of under-clamp.

It is unfortunate that in a certain number of cases the chest must be reopened after heart surgery. This may occur shortly after the operation has been performed, or perhaps several years later, as when the heart valve must be replaced. The dangers and difficulties of the original operation are increased by the necessity of reopening the chest cavity with its embedded sutures. These dangers and difficulties can be reduced by the use of a lower clamp such as illustrated in FIGS. 6, 7 and 8 which is shown in the form of a thin flexible strip 50 to which is attached from below individual clamps 10" of substantially the same size and shape as under-clamp 10'. These under-clamps 10" will cooperate with upper-clamps 10 in the same manner as described in connection with the form of invention illustrated in FIGS. 1-4 but in this case flexible strip 50 serves as a shield during reopening of the chest cavity, as more fully explained below.

Reopening of the chest requires substantially the same surgical procedure as in the original operation, i.e., first splitting the sternum, generally by sawing, but in such case, if it has been initially closed by the use of the closure shown in FIGS. 6 and 7, one will find the clamps in place similarly as shown in FIG. 3, except that strip 50 will be on the underside of the sternum.

With this picture in mind, the surgeon will open the skin 30, remove protective caps 30, and unscrew nut 26, and disengage upper clamps 10, all as shown in FIG. 3. In connection with the type of under-clamp as illustrated in FIG. 6, however, if the supporting rod is made flat-sided, as rod 20' shown in FIG. 7, it will be a simple procedure to unscrew such rod from the under-clamps 10". If then the sternum is resplit as by saw 60 (FIG. 8), the lower edge of the saw will ride along the top of strip 50 which will act to prevent penetration of the saw into the chest cavity and possible damage, for example to the heart itself.

The sternum having been split with under-clamps 10" however still in place, a hole 62 is drilled in the lower end of the sternum, and by means of a tool 64 inserted in such hole, the clamps 10" and strip 50 can be pried from the underside of the sternum and the rib cage spread apart for proceeding with the necessary surgery. The necessity of identifying and cutting a large number of wire sutures is thus avoided and greater safety in the overall reopening procedure results.

Various forms of sternum closures and the manner in which they may be used have thus been described. The drawings merely illustrate the principle of my invention, are not necessarily to scale, and variations in detail will be obvious to those skilled in this art and are deemed to be encompassed by this invention as defined by the claims which follow.

What I claim is:

1. Sternum closure device adapted to tightly hold together the split halves of a sternum, comprising a generally longitudinally extending support of a length substantially equal to the length of the sternum to be closed, a plurality of longitudinally spaced, threaded rods extending downwardly from said support, clamping means having sharp-edged upwardly extending arms supported by the lower ends of said rods and adapted to be positioned beneath the sternum, a plurality of reverse clamps having sharp-edged downwardly extending arms, each of said clamps having an enlarged central opening for mounting said clamps with free vertical movement on the respective rods above the sternum, and a threaded nut on each rod between said clamps and said support, whereby downward movement of each nut forces its corresponding clamp toward said clamping means with the sternum in between, and urges the corresponding sharp edges of the clamping means and said clamps into the sternum to hold the sternum halves together.

2. Sternum closure device according to claim 1, in which said clamping means comprise a plurality of individual clamps, one on the end of each rod.

3. Sternum closure device according to claim 2, in which the individual clamps forming said clamping means are each provided with an enlarged central section having an internally threaded bore into which each of said rods is individually screwed.

4. Sternum closure device according to claim 2, in combination with a thin flexible metallic strip extending the length of the sternum to be joined, and interconnecting the individual clamps beneath the sternum and interposed between said clamps and the underside of the sternum.

5. Sternum closure device according to claim 4, in which each of said threaded rods is flattened on opposite sides.

6. Sternum closure device according to claim 1, in which said longitudinally extending support includes a plurality of individual slides, one for each threaded rod, and means for mounting said slides for longitudinal movement along the length of said support.

7. Sternum closure device according to claim 6, in which said clamping means comprises a plurality of individual clamps, one on the end of each rod.

8. Sternum closure device according to claim 1, in which said clamping means comprises a strip adapted to extend the length of the sternum to be joined and having longitudinally spaced threaded openings for receiving the lower ends of said rods.

9. Sternum closure device according to claim 1, in combination with a plurality of nut-tightening devices loosely supported on said rod above each nut.

10. Sternum closure device according to claim 1, in combination with a thin piece of absorbable material threaded on each rod beneath each clamp for initially supporting each clamp on each rod.

11. Sternum closure procedure including the steps of supporting a plurality of longitudinally spaced threaded rods, each having a first upwardly directed clamping device at its lower end, a second freely supported downwardly directed clamping device intermediate its ends and a nut threaded on each rod above said second clamping device, pulling together the opposed portions of a split sternum with the first clamping devices positioned below the sternum and the second clamping devices positioned thereabove, tightening said nuts on said threaded rods against the second clamping devices to move said second clamping devices toward said first clamping devices with the sternum halves therebetween until the juxtaposed clamping devices are respectively tightly embedded in opposite sides of the sternum halves to hold the same together, cutting off each rod immediately above said nuts, and covering each nut and the cut-off portion of each rod with a smooth-surfaced cap.

* * * * *